United States Patent [19]

Philo

[11] Patent Number: 4,914,023

[45] Date of Patent: Apr. 3, 1990

[54] METHOD OF EXTENDING THE LINEAR RANGE OF AN ENZYME IMMUNOASSAY BY MEASURING OFF-PEAK ABSORBANCE

[75] Inventor: Roger Philo, Guilford, England

[73] Assignee: Serono Diagnostics Partners, Boston, Mass.

[21] Appl. No.: 58,483

[22] Filed: Jun. 5, 1987

[30] Foreign Application Priority Data

Jun. 10, 1986 [GB] United Kingdom ................. 8614084

[51] Int. Cl.$^4$ ................... G01N 33/53; G01N 33/543; G01N 33/536
[52] U.S. Cl. .......................................... 435/7; 435/18; 435/21; 436/500; 436/518; 436/536; 436/548; 436/818
[58] Field of Search ............... 435/7, 18, 21; 436/530, 436/500, 548, 818, 518, 536

[56] References Cited

U.S. PATENT DOCUMENTS

| | | |
|---|---|---|
| 4,496,658 | 1/1985 | Kondo et al. |
| 4,672,028 | 6/1987 | Olson ........................................ 435/5 |
| 4,690,890 | 9/1987 | Loor et al. ............................... 435/7 |

OTHER PUBLICATIONS

"Methods of Enzymatic Analysis", 3rd Edition, vol. X, Antigens and Antibodies 1, VCH Publishers, Weinheim, FRG, May 1986, Bergmeyer, editor.

"Clinical Diagnosis and Management by Laboratory Methods" J. B. Henry, editor; Saunders, Philadelphia, 1979, p. 86.

*Primary Examiner*—Robert J. Warden
*Assistant Examiner*—Jack Spiegel
*Attorney, Agent, or Firm*—Stephan P. Williams

[57] ABSTRACT

The present invention relates to enzyme immunoassays employing one or more enzyme label-substrate pairs which give rise to colored products and in which absorption by the product of substrate conversion by at least one enzyme label at a first wavelength, at or close to the optimum wavelength for absorbance, exceeds the linear range of the detector, which immunoassay includes the steps of measuring the said substrate conversion at a second wavelength at which absorbance by the relevant product is significantly lower than at the said first wavelength and calculating the true absorbance at the said first wavelength by utilizing the result of linear regression analysis of absorbance measurements obtained with product standards at the said first and second wavelengths within the linear range of the detector.

8 Claims, 8 Drawing Sheets

FIG. 1

FIG. 2

2-SITE IEMA

| LOW LIGAND | | HIGH LIGAND |
|---|---|---|
|  | LIGAND IN SAMPLE OR STANDARD (e.g. TSH OR HCG) |  |
| | + | |
|  | ANTI-LIGAND-HAPTEN CONJUGATE (e.g. ANTI-LIGAND-FITC) |  |
| | + | |
|  | ENZYME-ANTI-LIGAND CONJUGATE |  |

ADD ANTI-HAPTEN SOLID PHASE

LOW SIGNAL            HIGH SIGNAL

METHOD OF EXTENDING THE LINEAR RANGE OF AN ENZYME IMMUNOASSAY BY MEASURING OFF-PEAK ABSORBANCE

The present invention relates to methods of immunoassay of antigens and to kits for carrying out such methods. In particular, it relates to improvements in immunoassays which employ enzymelabelled antibodies to quantify the antigen under assay (hereinafter referred to as enzyme immunoassays).

Conventional enzyme immunoassays suffer from the problem that it is difficult to have high sensitivity together with a wide assay range. The problem is caused by the limited dynamic range of the signal detection system. Considering for example a 2-site enzyme immunoassay, for high sensitivity a marked increase in signal is required for a unit increase in analyte concentration, but at high analyte concentrations the signal can be greater than the dynamic range of the measurement system. If the signal intensity at high analyte concentrations is reduced to be within the dynamic range of the detection instrument, then the signal change for a unit increase at low analyte concentrations will be reduced and assay sensitivity decreased. The problem is particularly acute for enzyme immunoassays utilising spectrophotometric end-point detection.

We have now devised a means of carrying out enzyme immunoassays employing enzyme labels capable of converting a substrate to a coloured product whereby this problem is overcome.

According to one aspect of the present invention, we provide an enzyme immunoassay employing one or more enzyme label-substrate pairs which give rise to coloured products and in which absorption by the product of substrate conversion by at least one enzyme label at a first wavelength, at or close to the optimum wavelength for absorbance, exceeds the linear range of the detector, which immunoassay includes the steps of measuring the said substrate conversion at a second wavelength at which absorbance by the relevant product is significantly lower than at the said first wavelength and calculating the true absorbance at the said first wavelength by utilizing the result of linear regression analysis of absorbance measurements obtained with product standards at the said first and second wavelengths within the linear range of the detector.

Selection between the two chosen wavelengths for a particular enzyme-substrate pair thereby enabling the requirement for high sensitivity or wide assay range to be met may conveniently be achieved automatically with appropriate instrumentation The technique of the present invention is applicable to any of the known types of enzyme immunoassays wherein enzyme-substrate pairs giving rise to coloured products are employed, e.g. 2-site enzyme immunoassays, including 2-site enzyme immunoassays of the indirect-link type analogous to the radioimmunometric assays described in our co-pending European published application No. 105714 (hereinafter referred to as 2-site IEMAs); 1-site enzyme immunoassays, including 1-site enzyme immunoassays of the indirect-link type described in our co-pending European application No. 85306272.7 (hereinafter referred to as 1-site IEMAs); and dual analyte enzyme immunoassays wherein two sets of antibodies labelled with different enzymes are employed to enable measurement of two antigens in a single sample. Examples of a 1-site IEMA and a 2-site IEMA are illustrated schematically in FIGS. 1 and 2 respectively of the accompanying Figures.

For a better understanding of the present invention, more detailed consideration will now be given to use of the enzyme-substrate pair alkaline phosphatase/phenolphthalein monophosphate in a 2-site enzyme immunoassay (commonly referred to as a sandwich immunoassay).

In a conventional 2-site enzyme immunoassay, the antigen under assay (hereinafter referred to as the analyte) which must have two or more epitopes, is insolubilised by reaction with an unlabelled antibody conjugated to a solid phase and reacted with an enzymelabelled antibody directed to a different (preferably roomly-spaced) epitope of the analyte. The quantity of labelled antibody which becomes immobilised due to the complexing reaction is directly proportional to the amount of analyte present in the sample.

2-site enzyme immunoassays of the indirect-link type (2-site IEMAs) employ two soluble antibody reagents directed to different epitopes of the analyte, one soluble antibody reagent comprising enzyme-labelled antibody molecules. The solid phase employed is conjugated to a further reagent which is capable of specifically non-covalently binding the non-labelled antibodies. These antibodies may, for example, conveniently be conjugated to a reagent X as in the assay illustrated in FIG. 2. The separation step is then achieved by using a solid phase conjugated to a specific binding partner for reagent X.

When using such an assay system, increasing analyte concentration will result in increasing phenolphthalein concentration.

Figure 3:
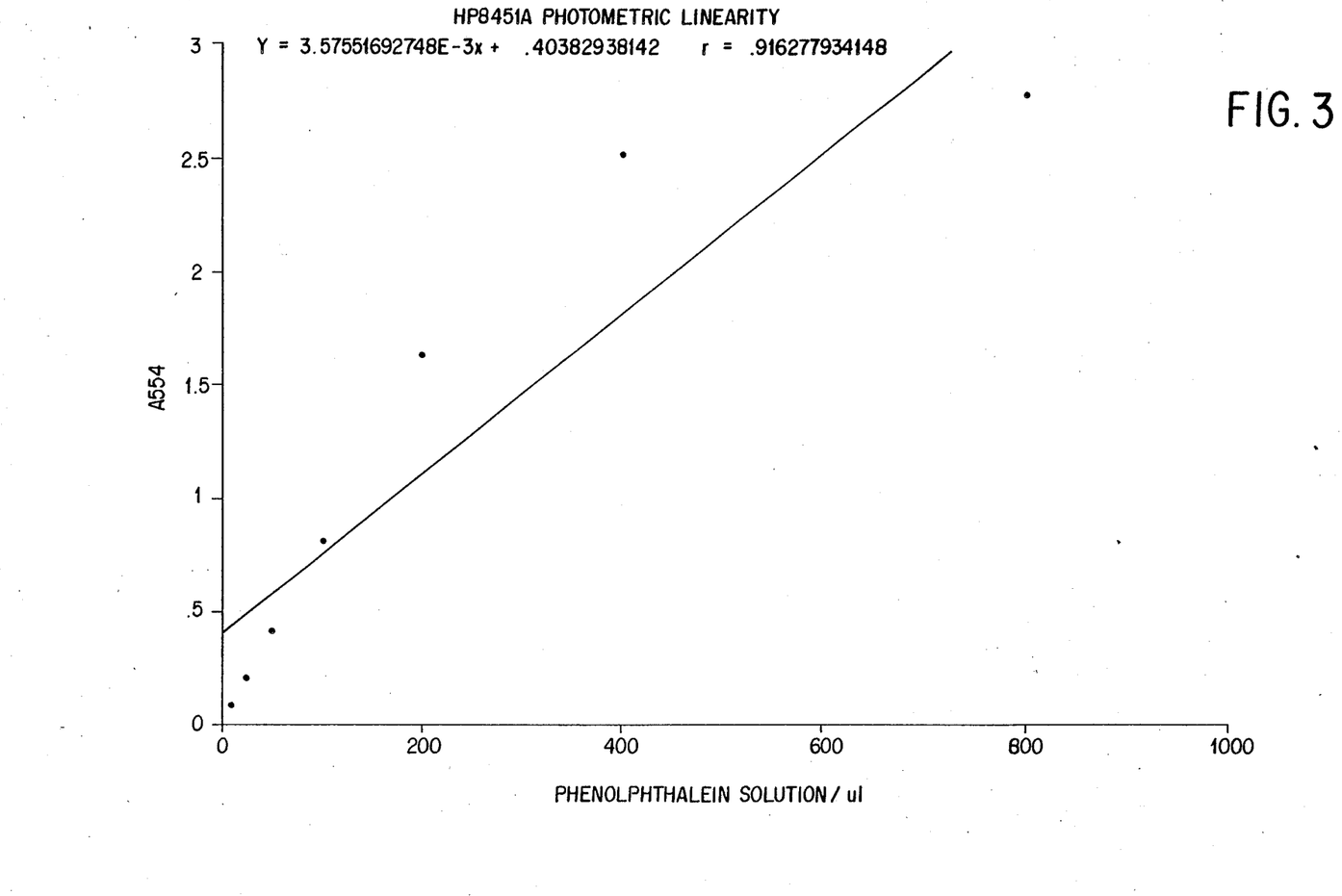
Figure 4:
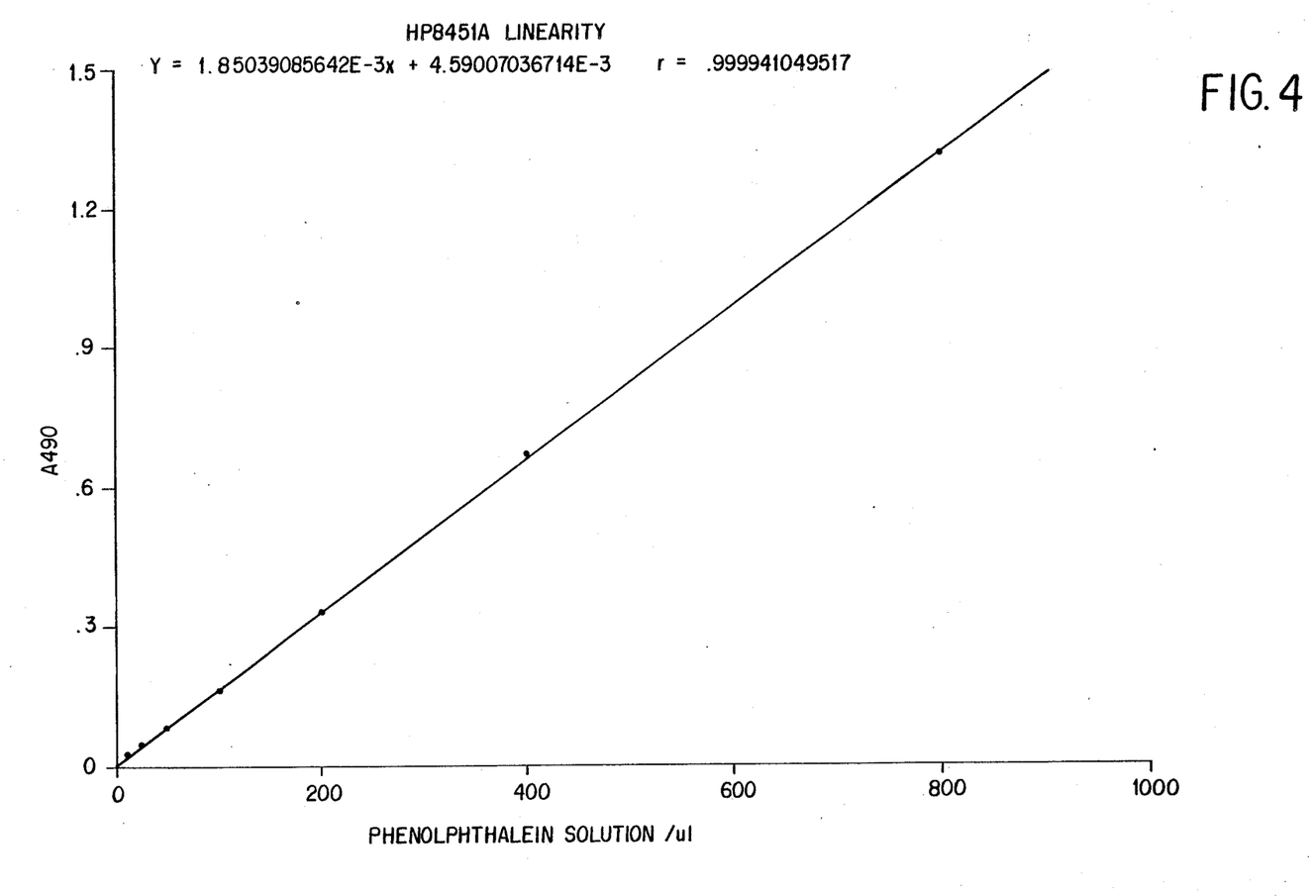
Figure 5:
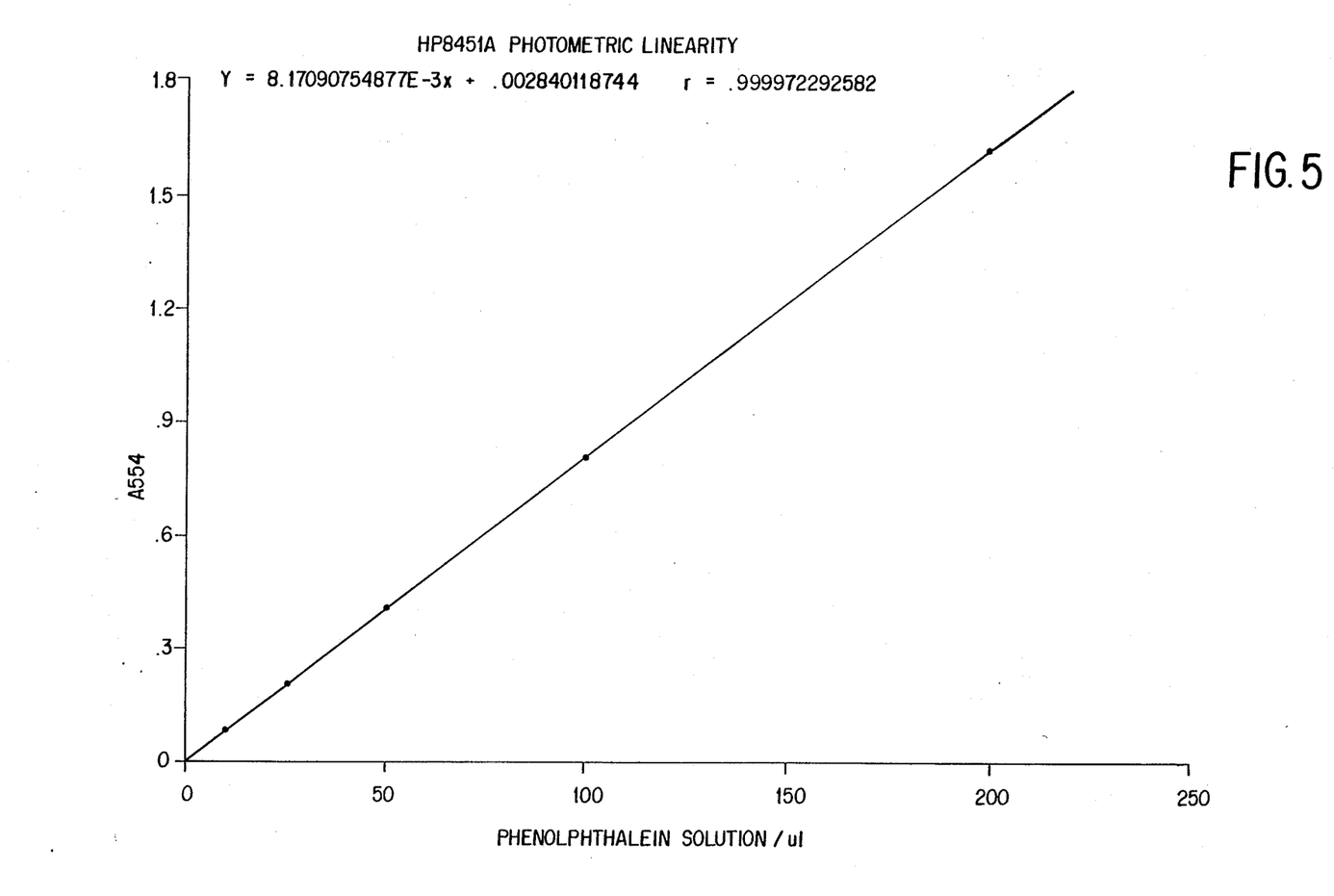
Figure 6:
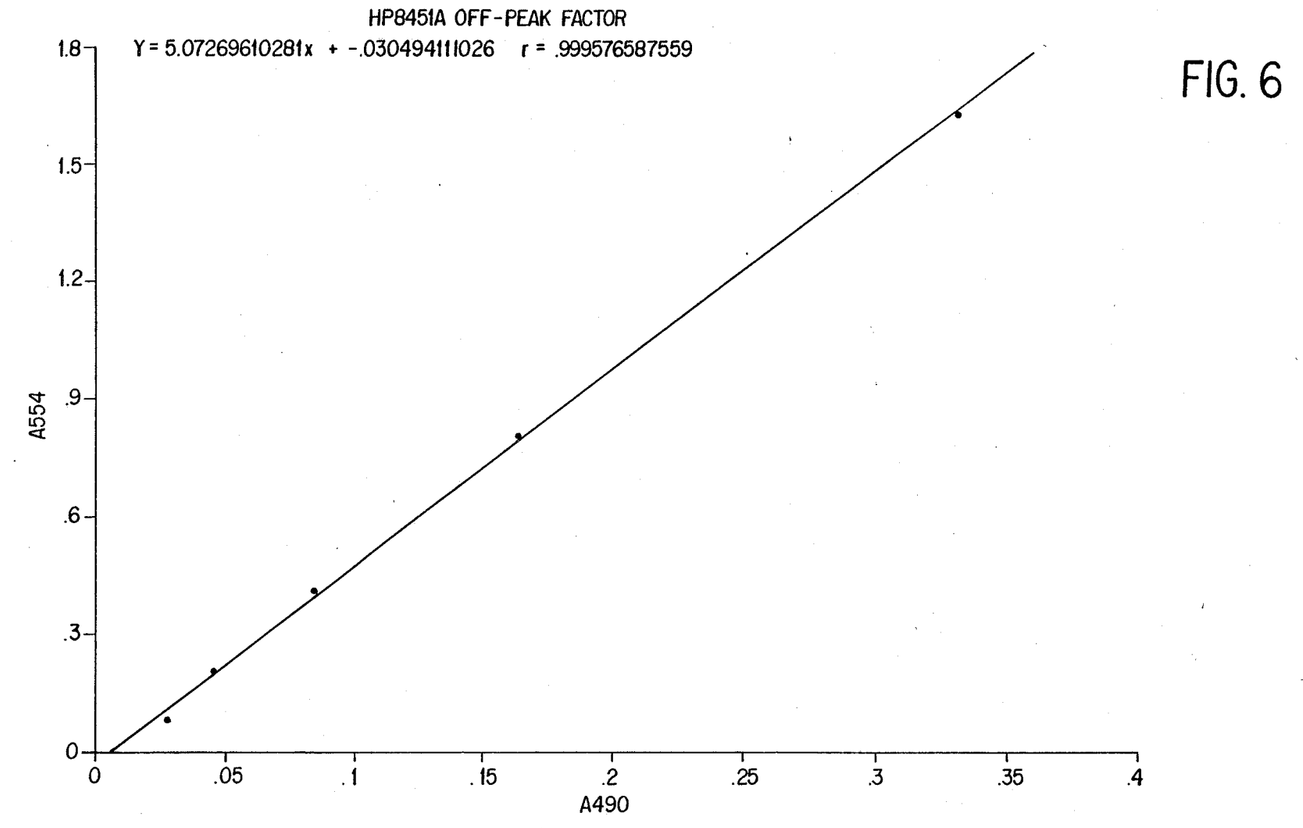

The data in FIG. 3 models this by showing how phenolphthalein concentration (here expressed as volume of phenolphthalein solution in a fixed total volume) is related to absorbance at 554 nm (the peak visible absorbance for phenolphthalein) when this is measured using a Hewlett-Packard Spectrophotometer. It can be seen that measured absorbance is not linear with concentration above $A_{554}$ values of about 1.6 and that above $A_{554}$ values of 2.5 changes in phenolphthalein concentration produce very little change in $A_{554}$. However if the absorbances at 490 nm (a suitable off peak wavelength) of the same solutions are measured the entire concentration range shown in FIG. 3 is within the linear range of the instrument (FIG. 4). This data can be used to calculate $A_{554}$ values above the linear range of the instrument by carrying out a linear regression analysis of $A_{554}$ on $A_{490}$ for those solutions whose $A_{554}$ values fall within the linear range (FIGS. 5 and 6). The slope of this regression is the factor by which $A_{490}$ values are to be multiplied to obtain $A_{554}$ values if these are above the linear range of the instrument.

The enzyme substrate pair alkaline phosphatase/phenolphthalein monophosphate may also be used in a dual analyte enzyme immunoassay according to the present invention together with, for example, β-galactosidase and p- and/or o-nitrophenyl-β-D-galactoside, o- or p-nitrophenol being independently detectable in the presence of phenolphthalein by absorbance measurement. Thus, for example, o- or p-nitrophenol may be measured at 404 nm and a second wavelength at which absorbance is lower, and phenolphthalein may be measured at 554 nm or about 490 nm. Preferably, conditions for the enzyme reaction step will be chosen so that the two enzyme reactions proceed simultaneously. A suitable buffer for such a "combo" immunoassay will, for example, be within the pH range 8.5–8.7 and comprise about 0.25M to 1M diethanolamine, about 3–10 mM phenolphthalein and about 50 mM p-nitro-phenyl-β-D-galactoside.

Assays of this type are described inter alia in the accompanying Examples which are intended to illustrate the present-invention further.

EXAMPLE 1

Validation of off-peak measurement for high O.D. samples using alkaline phosphatase solutions Alkaline phosphatase solutions of known concentrations ranging from 0.005 U/ml to 5 U/ml were made up, as were 5 alkaline phosphatase solutions of "unknown" concentrations in this range. To 10 μl of each of these solutions, were added 300 μl of 3 mM phenolphthalein phosphate in substrate buffer (1M diethanolamine, 0.15M NaCl, 1 mM MgCl$_2$, pH 8.6). After 15 min. at 37° C., 1 ml of stop solution (200 mM Na$_2$CO$_3$, 200 mM EDTA, 20 mM Na$_3$PO$_4$ adjusted to pH 12 and a further 100 mM NaOH added) was added and A$_{490}$ and A$_{554}$ measured. When A$_{554}$ was greater than 1.5 the solutions were diluted 10 fold with a mixture of substrate buffer and stop solution in the ratio 0.3:1 and remeasured.

Results

Plots of enzyme concentration against A$_{554}$ and A$_{490}$ were used to obtain estimates of the enzyme concentration in the unknown samples. Where A$_{554}$ values were above 1.5 the value used was calculated from that of the 10 fold dilution.

| Sample | enzyme conc. A$_{490}$ | (U/ml) calculated from A$_{554}$ |
|---|---|---|
| 1 | 3.04 | 3.30 |
| 2 | 3.80 | 3.90 |
| 3 | 1.20 | 1.22 |
| 4 | 0.66 | 0.68 |
| 5 | 1.78 | 1.84 |

Regression of the enzyme concentrations calculated from A$_{554}$ on enzyme concentrations calculated from A$_{490}$ values gave: $-y = -0.011 + 1.051x$; $r = 0.999$

EXAMPLE 2

Validation of off-peak measurement for high O.D. samples in a 2-site IEMA for human chorionic gonadotrophin (HCG)

(i) Preparation of reagents (a) anti-βsubunit HCG—alkaline phosphatase and anti-whole HCG—alkaline phosphatase Monoclonal antibodies against β-subunit and whole HCG were labelled with alkaline phosphatase using the following method:

0.16 ml N-succinimidyl 4-(N-maleimidomethyl) cyclohexane-1-carboxylate (SMCC) (60 mM in dimethylformamide-DMF) was added to 1.6 ml of alkaline phosphatase (2 mg/ml in 50 mM sodium borate, 1 mM magnesium chloride and 0.1 mM zinc chloride, pH 7.6) and incubated for 1 hour at 30° C. The enzyme was separated by passage through a Sephadex G-25 medium column (1×35 cm) equilibrated in 0.1 M pH 7.0. The purified enzyme was stored at +4° C. until required.

16.3 μl of N-succinimidyl 3-(2-pyridyldithio) propionate (SPDP) (25 mM in ethanol) were added to 1 ml of monoclonal antibody (3 mg/ml in 200 mM sodium propionate, pH 6.0) and incubated for 30 minutes at room temperature. The antibody was separated by passage through a disposable Sephadex G-25 column (PD-10) equilibrated in 200 mM sodium acetate buffer, pH 4.5. Dithiothreitol (1 M) was added to the antibody (1/20 of antibody volume added) and left for 10 minutes at room temperature. The antibody was de-salted using a Sephadex G-25 medium column (1×35 cm) equilibrated in 200 mM sodium propionate, pH 6.0.

Antibody and alkaline phosphatase prepared as above were mixed in an equimolar ratio and left to conjugate for 24 hours at 4° C. The resulting conjugate was purified by high performance liquid chromatography (HPLC) on a TSK 3000 SW column equilibrated in 200 mM sodium propionate, 1 mM magnesium chloride and 0.1 mM zinc chloride at pH 6.0.

(b) anti-βsubunit HCG—fluorescein isothioyyanate (FITC)

A population of monoclonal antibodies directed against the β-subunit of HCG was labelled with fluorescein isothiocyanate (FITC) using the following method:

200 μg of FITC (Sigma London Chemical Co., England) was reacted with 5 mg antibody in 1.4 ml sodium bicarbonate buffer, 0.2M, pH 9.0 for 18 hours at root temperature. The reaction mixture was purified by gel filtration on Sephadex G-50 superfine, giving a product incorporating an average of 6 molecules FITC per antibody molecule.

(c) anti-FITC antibody covalently coupled to magnetisable solid phase.

Anti-FITC was a conventional polyclonal antiserum obtained by immunising sheep with FITC conjugated to keyhole limpet haemocyanin. The magnetisable cellulose particles were a composite of cellulose containing approximately 50% black ferric(ous) oxide (Fe$_3$O$_4$), with mean particle diameter of 3 microns (see Forrest and Rattle, "Magnetic Particle Radioimmunoassay" in Immunoassays for Clinical Chemistry, p. 147–162, Ed Hunter and Corrie, Churchill Livingstone, Edinburgh (1983)). Anti-FITC antiserum was covalently coupled to the magnetisable cellulose following cyanogen bromide activation of the cellulose, according to the procedure of Axen et al., Nature 214, 1302–1304 (1967). The antiserum was coupled at a ratio of 2 ml antiserum to 1 gram of magnetisable solid phase. The solid phase was diluted to 5 mg/ml in mM Tris/HCl buffer, pH 8.0, containing 0.1% sodium azide, 0.5% bovine serum albumin (BSA), fraction V, 0.25% Tween 20 and 0.5% methocell.

(d) Preparation of the substrate buffer. The substrate buffer consisted of a 1M solution of diethanolamine containing 0.9% (w/v) NaCl, 1 mM MgCl$_2$, 1.543 mg/ml phenolphthalein monophosphate disodium salt or 2.02 mg/ml phenolphthalein monophosphate di(cyclohexylammonium) salt at pH 8.6.

(e) Preparation of the wash buffer. The wash buffer consisted of 0.9% sodium chloride in 10 mM Tris/HCl, pH 8.6.

(f) Preparation of the stop solution. The stop solution was prepared by adjusting a solution containing 200 mM EDTA, 200 mM Na$_2$CO$_3$ and 20 mM Na$_3$PO$_4$ to pH 12 and then adding 100 mM NaOH.

(g) Preparation of the assay buffer. The assay buffer consisted of 0.5% bovine serum albumin (fraction v), 0.2% sheep serum, 1 mM MgCl$_2$ 0.1 mM ZnCl$_2$, 0.1M sodium chloride and 0.2% sodium azide in 0.1M Tris/HCl, pH 8.0.

(h) Preparation of the HCG Standards. Standard HCG solutions were prepared by adding approximately the required concentration of purified HCG (obtained as a freeze dried preparation from Biodata SpA, Italy) in normal male human serum and determining the exact concentration by assaying using a HCG MAIAclone kit (Serono Diagnostics Limited) against working reference preparations of HCG which themselves had been calibrated against the First International Reference Preparation (75/537).

(ii) Protocol

100 μl of sample or standard and 250 μl tracer (50 ng anti-β-subunit HCG-alkaline phosphatase, 100 ng anti-whole HCG-alkaline phosphatase, 800 ng anti-β-subunit HGG-FITC and 300 ng anti-LH (luteinising hormone)) were mixed and incubated for 15 mins at 37° C. 200 μl of magnetisable anti-FITC solid phase was added to each tube, followed by mixing and incubation at 37° C. for a further 5 mins. The solid phase was separated magnetically, the supernatant decanted and 500 μl of wash buffer added to each tube. After mixing, the solid phase was again separated magnetically. This washing procedure was repeated twice more and, after the final wash, the tubes were inverted and allowed to drain for 5 mins.

300 μl of substrate buffer was added to each tube, mixed, and the tubes incubated at 37° C. for 15 mins. 1 ml of stop solution was then added to each tube. The magnetisable particles were sedimented magnetically for 10 minutes and the absorbances of the supernatants read at 490 nm or 554 nm, directly or after dilution.

The results obtained were compared with those obtained using a HCG MAIAclone kit.

(iii) Results

Table 1 shows the results obtained when high ($>1.5$) OD samples from an HCG IEMA were treated in two different ways. Results in the column labelled 1/10 dilution were obtained by diluting all tubes (standards and unknowns) where $A_{554} > 1.5$ to 1/10 in a mixture of substrate/stop in the ratio 0.3:1. Undiluted $A_{554}$ values were calculated from these.

Results from the column labelled off peak were obtained by measuring at 490 nm all tubes whose $A_{554} > 1.5$ and calculating $A_{554}$ fromn $A_{490}$ by multiplying by the slope of the linear regression analysis as in FIG. 4. These results are in good agreement.

Table 2 shows a linear regression analysis of results from HCG IEMA (off peak calculation for high OD) with HCG MAIAclone and a linear regression of results from HCG IEMA (dilution of high O.D. samples) with HCG MAIAclone. In both cases the results are in good agreement.

Figure 7:
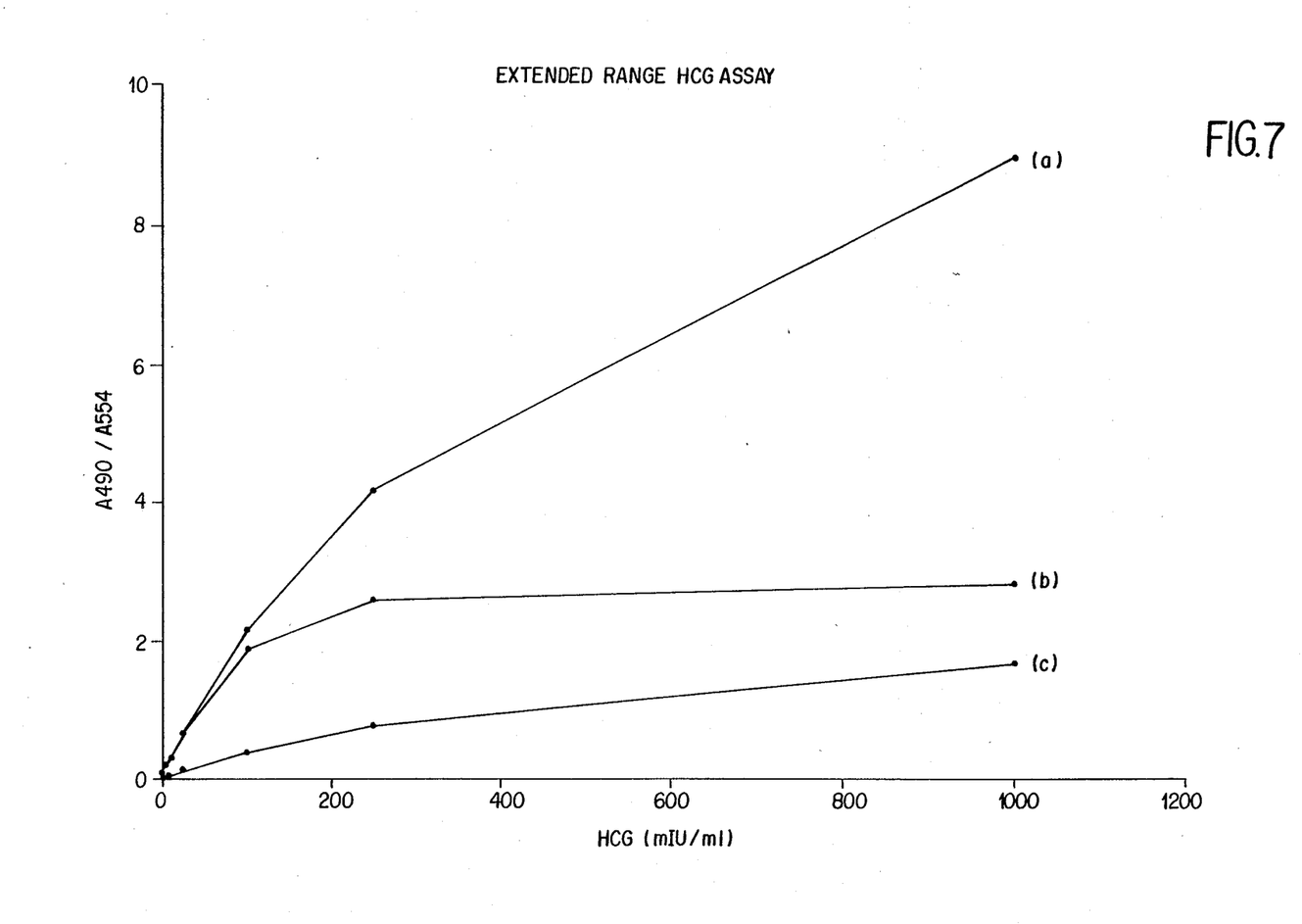

FIG. 7 shows the results from an HCG IEMA. Curve (b) gives $A_{554}$ values as measured using a Hewlett-Packard 8451A spectrophotometer. The detection limit for this assay calculated from $A_{554}$ values is 0.36 mIU/ml, but the response is very flat above 250 mIU/ml.

Curve (c) shows $A_{490}$ values. These give a response usable up to 1000 mIU/ml, but a detection limit of 0.9 mIU/ml. Curve (a) shows measured $A_{554}$ values below $A_{554}=1.5$ an values calculated from $A_{490}$ for those above. This curve combines the advantages of low detection limit and extended range.

TABLE 1

|  | 1/10 Dilution | Off Peak |
|---|---|---|
| Sample 1 | 499 | 499 |
| 2 | 280 | 255 |
| 3 | 141 | 128 |
| 4 | 62 | 62 |

TABLE 1-continued

|  | 1/10 Dilution | Off Peak |
|---|---|---|
| 5 | 30 | 33 |
| 6 | 14.5 | 15.5 |
| 7 | 550 | 580 |
| 8 | 300 | 280 |
| 9 | 160 | 151 |
| 10 | 66 | 70 |
| 11 | 33.5 | 36 |
| 12 | 16.5 | 18.5 |
| 13 | 7.5 | 8.5 |
| 14 | 530 | 560 |
| 15 | 315 | 290 |
| 16 | 165 | 155 |
| 17 | 81 | 83 |
| 18 | 31 | 33.5 |
| 19 | 14.5 | 17 |
| 20 | 840 | 850 |
| 21 | 430 | 430 |
| 22 | 230 | 210 |
| 23 | 109 | 107 |
| 24 | 48 | 32 | n = 24
r = 0.9982
i = −4.34 mIU/ml
slope = 1.015

TABLE 2

(a) correlation with MAIAclone, pregnant samples off peak n = 108
r = 0.9938
slope = 1.019
i = −1.015 mIU/ml (b) correlation with MAIAclone diluted IEMA n = 20
r = 0.999
slope = 1.048
i = −1.208 mIU/ml

EXAMPLE 3

A simultaneous dual analyte enzyme immunoassay for $T_4$ and TSH

Figure 1:
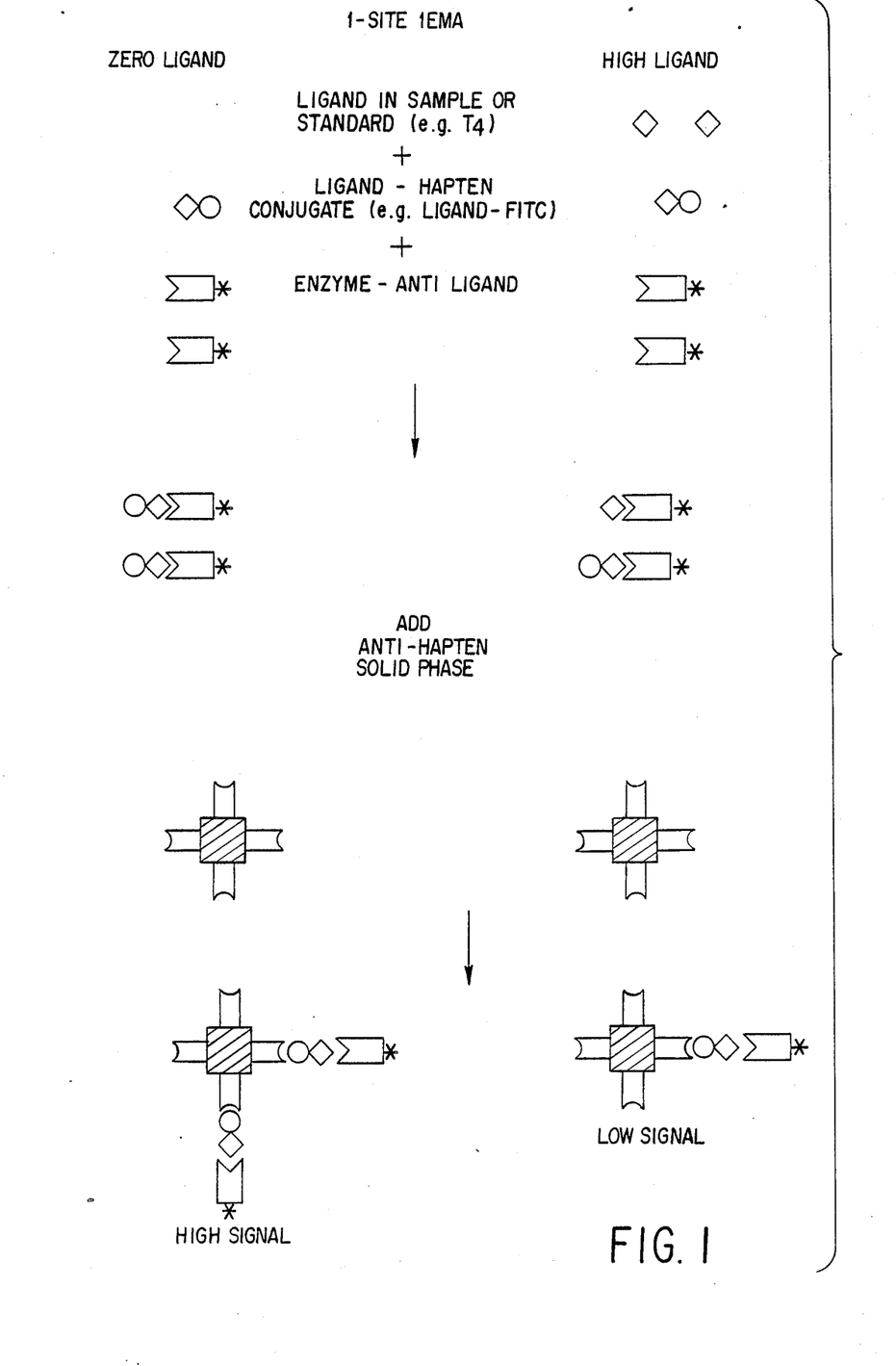
Figure 2:
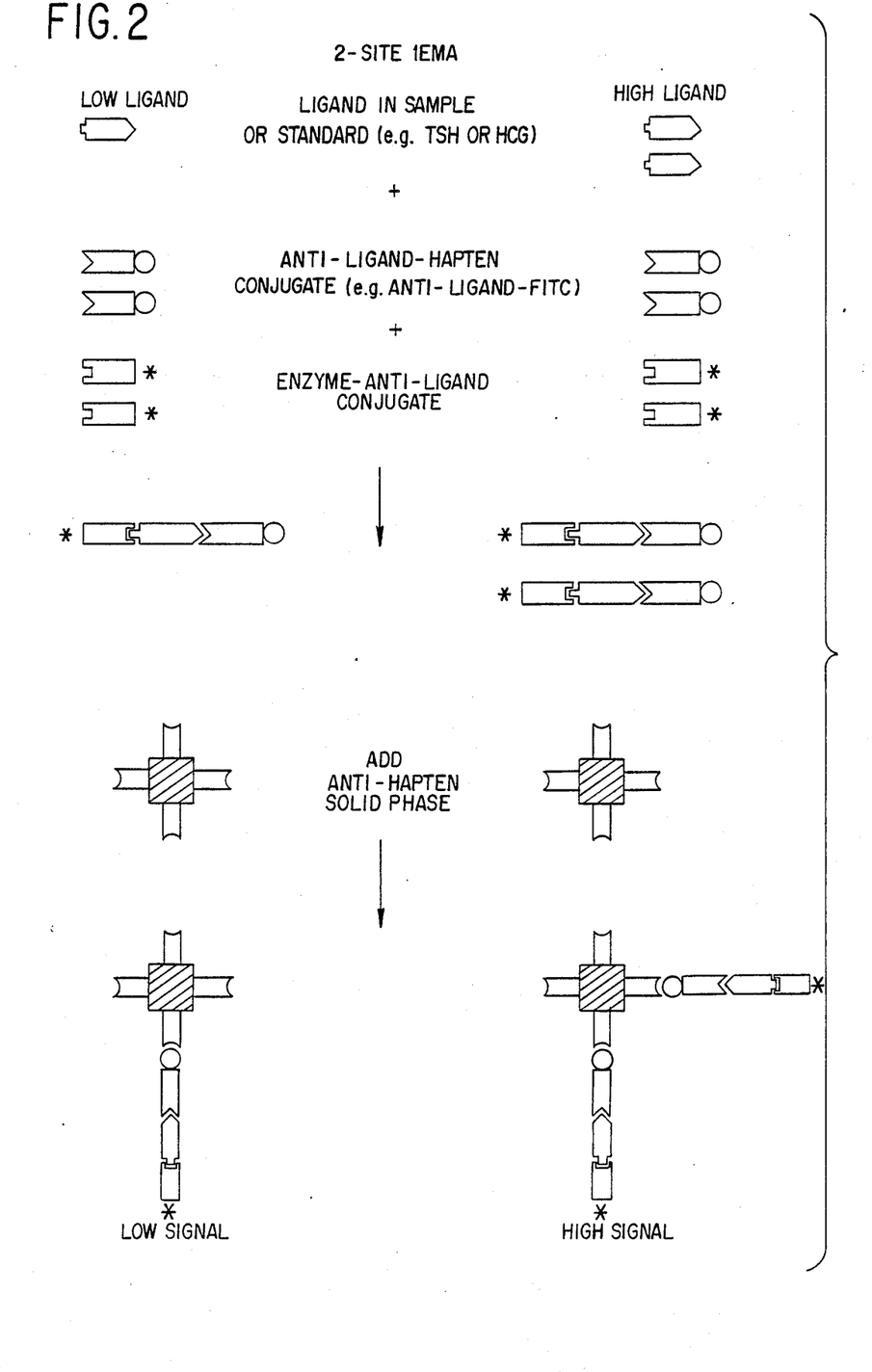

In this Example, a 1-site indirect-link enzyme immunoassay for thyroxine as illustrated schematically in FIG. 1 was combined with a 2-site indirectlink enzyme immunoassay (i.e. an indirect link sandwich immunoassay) for thyroid-stimulating hormone (TSH) as illustrated schematically in FIG. 2.

(i) Preparation of monoclonal antibodies

Monoclonal antibodies to $T_4$ and TSH were obtained from mouse ascites fluid by the process reported by Kohler and Milstein in Nature 256 (1975) 495–497. Antibodies from individual hybridoma cell lines were screened to identify those producing antibody to discrete antigenic determinants. Those antibodies with the highest affinities for the antigens in question were selected for use in the assay.

(ii) Preparation of antibody reagents (a) anti-TSH—alkaline phosphatase

Two populations of monoclonal antibodies directed to different epitopes of TSH were labelled with alkaline phosphatase using the same method as used in Example 2 to prepare the anti-HCG-alkaline phosphatase conjugate. Binding of one alkaline phosphatase-labelled monoclonal antibody to TSH did not interfere with the binding of the other enzyme-labelled monoclonal antibody.

(b) anti-$T_4$β-galactosidase

150 μl of SPDP (25 mM in ethanol) was added to 9.4 ml of anti-T4 antibody at 100 μg/ml in 0.2M sodium propionate buffer at pH 6.0 and incubated at room temperature for 30 minutes. The resulting antibody was then purified by passage down an HPLC TSK 3000 SW column equilibrated in sodium propionate buffer (0.02 M, pH 6.0). The antibody thus obtained was then mixed with an equimolar concentration of β-galactosidase and incubated overnight at 4° C. before purification on a TSK 4000 column equilibrated in sodium propionate buffer (0.2 M, pH 6.0).

(c) anti-TSH-FITC

A further population of anti-TSH monoclonal antibodies, directed to a third epitope of TSH, was conjugated with FITC using the same method as in Example 2(i)(b).

(iii) Preparation of FITC-T4.

The conjugate FITC-T4 was prepared and purified by the method of Smith in FEBS Letters 77 25 (1977).

(iv) Preparation of the solid phase reaqent.

As in Example 2(i)(c)

(v) Preparation of the substrate buffer

The substrate buffer consisted of a 1M solution of diethanolamine containing 150 mM NaCl, 1 mM MgCl$_2$, 3 mM phenophthalein monophosphate and 50 mM p-nitrophenyl-β-D-galactoside at pH 8.6.

(vi) Preparation of the stop solution

The stop solution was prepared by adjusting a solution containing 200 mM Na$_2$CO$_3$, 20 mM Na$_3$PO$_4$ and 300 mM EDTA to pH12 and then adding NaOH to 150 mM.

(vii) Preparation of assay reagents

A cocktail of reagents (Reagent A) was prepared consisting of FITC-T4 (10.5 pM), anti-TSH antibody conjugated to FITC (5 μg/ml), anti-TSH antibody conjugated to alkaline phosphatase (1 μg/ml) and 8-anilino-1-naphthalene sulphonic acid (1.5 mg/μl) in assay buffer (100 mM Tris/HCl) buffer containing 0.5% bovine serum albumin (fraction V), 0.2% sheep serum, 0.2% sodium azide, 100 mM sodium chloride, lmM magnesium chloride and 0.1 mM zinc chloride at pH 8.0).

The second reagent (Reagent B) consisted of anti-T4 antibody conjugated to β-galactosidase (7.61 μg/ml) in assay buffer.

(viii) T4/TSH Assay Protocol

To 100 μl of sample, 200 μl of reagent A and 100 μl of reagent B were added. After vortexing, the assay was incubated at 37° C. for 20 minutes, followed by the addition of 200 μl anti-FITC solid phase (5 mg/ml). After a 5 minute incubation at 37° C., the assay was separated magnetically and the supernatant removed by decantation. The magnetic particle solid phase was washed three times by adding 500 μl of wash buffer (10 mM Tris/HCl containing 0.9% sodium chloride at pH 8.6), vortexing and separating magnetically, followed by decanting the solid phase was drained for two minutes. Upon addition of 300 μl substrate solution, the tubes were incubated at 37° C. for 20 minutes and then 1 ml of stop solution added. After the solid phase had been sedimented magnetically for at least 15 minutes, the concentration of T4 was calculated from A$_{404}$ of the supernatant. The concentration of TSH wa calculated from the absorbance of the supernatant at 554 nm or 490 nm.

(ix) Results

Figure 8:
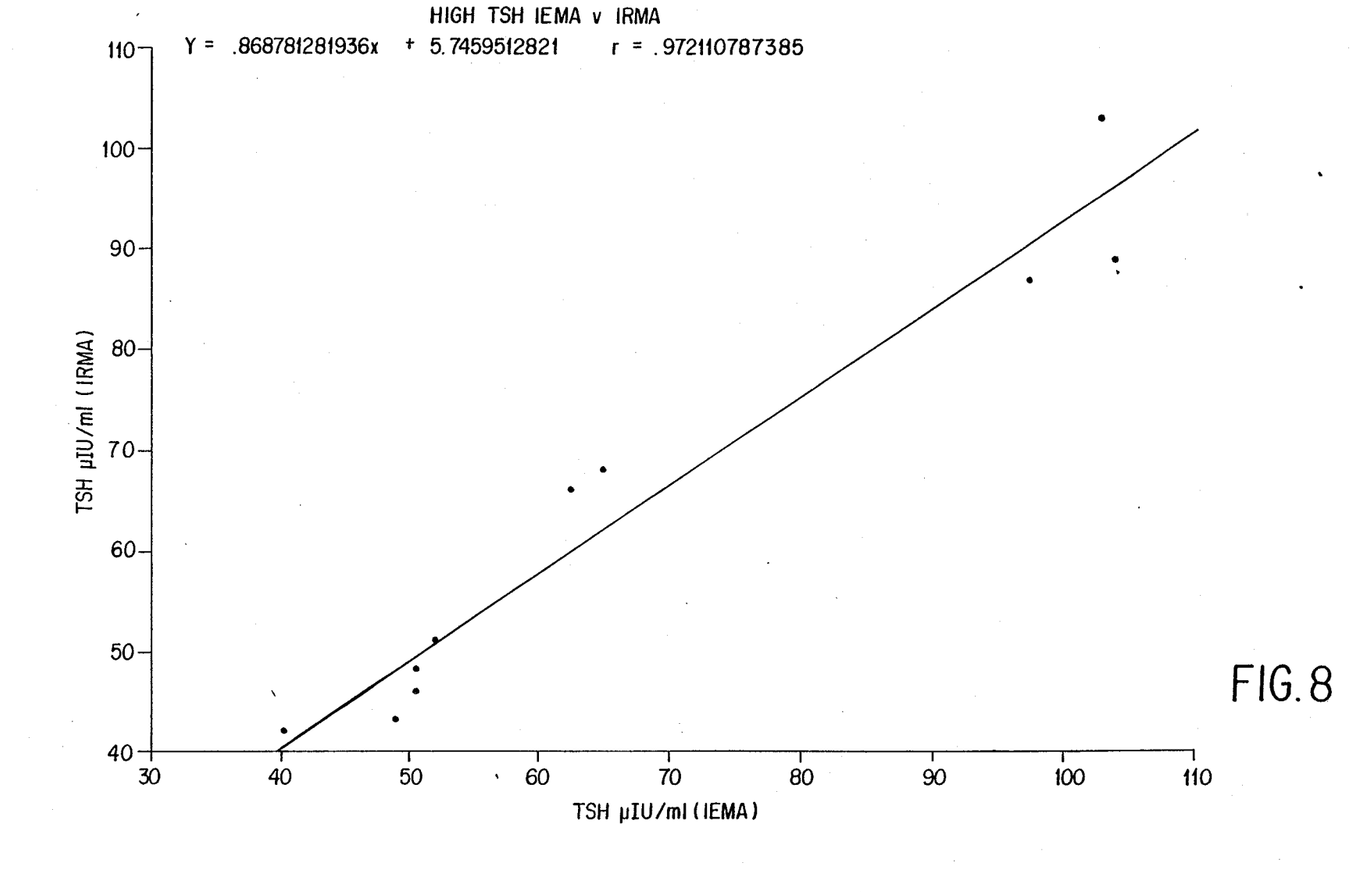

FIG. 8 shows a comparison of results obtained for TSH in samples using the above protocol and using a 2-site radiometric (mmunoassay of the indirectlink type as described in published European application No. 105714 (IRMA assay).

I claim:

1. In an enzyme immunoassay which quantifies a substance under assay by measuring absorbance of a colored product formed by substrate conversion of an enzyme label-substrate pair, the improvement comprising extending the linear range of said immunoassay without reducing its sensitivity by measuring absorbance at or near the peak wavelength for absorbance measurements for that enzyme label-substrate pair and measuring absorbance at an off-peak wavelength, at which absorbance is significantly lower than at the peak wavelength, when said absorbance measurement at the peak wavelength exceeds the linear range of the measuring technique employed, then determining the quantities of said substance under assay by comparing said measurements to a standard composite curve which plots absorbance at both peak and off-peak wavelengths versus known quantities of said substance.

2. The enzyme immunoassay of claim 1 wherein the enzyme label-substrate pair is selected from β-galactosidase/nitrophenyl-β-D-galactoside and alkaline phosphatase/phenolphthalein monophosphate.

3. The enzyme immunoassay of claim 1 wherein the enzyme label-substrate pair is alkaline phosphatase/phenolphthalein monophosphate and the off-peak wavelength at which absorbance is measured is 490 nm.

4. The enzyme immunoassay of claim 1 comprising a dual analyte enzyme immunoassay wherein a different enzyme label-substrate pair is employed for quantifying each analyte.

5. The enzyme immunoassay of claim 4 wherein the enzyme label-substrate pairs employed are alkaline phosphatase/phenolphthalein monophosphate and β-galactosidase/nitrophenyl-β-D-galactoside.

6. An enzyme immunoassay as claimed in claim 5 wherein both enzyme reactions proceed simultaneously in the presence of a substrate buffer solution at pH 8.5–8.7 initially comprising 0.25 to 1M diethanolamine, 3–10mM phenolphthalein and about 50mM p-nitrophenyl-β-D-galactoside.

7. An enzyme immunoassay as claimed in claim 6 for simultaneous assay in a single liquid sample of thyroxine (T4) and thyroid-stimulating hormone (TSH), which comprises the steps of:

(a) mixing said sample with
  (i) two populations of alkaline phosphatase-labelled monoclonal antibodies directed to different epitopes of TSH,
  (ii) a population of β-galactoside-labelled monoclonal
  antibodies directed to an epitope of T4,
  (iii) a population of monoclonal antibodies directed to a third epitope of TSH and conjugated to fluorescein isothiocyanate (FITC), and
  (iv) an FITC-T4 conjugate;
(b) adding to the assay system a solid phase having bound thereto an i-FITC antibodies;
(c) after a suitable incubation time separating said solid phase from the liquid phase;
(d) incubating the separated solid phase in the presence of said substrate buffer and stopping the enzyme reactions after a suitable length of time;
(e) measuring the absorbance of the supernatant at 404 nm and 490 nm;

(f) calculating the true absorbance of the supernatant at 554 nm attributable to the presence of phenolphthalein by utilizing the result of linear regression analysis of absorbance measurements obtained with phenolphthalein standards at 490 nm and 554 nm within the linear range of the detector; and (g) determining from said calculated absorbance at 554 nm and the measured absorbance at 404 nm the amounts of TSH and T4 respectively in said sample.

8. An enzyme immunoassay as claimed in claim 4 for measuring human chorionic gonadotrophin (HCG) and free HCG-$\beta$ subunit in a liquid sample which comprises the steps of:

(a) mixing said sample with
  (i) anti-$\beta$ subunit HCG monoclonal antibodies and anti-HCG monoclonal antibodies directed against a non-$\beta$ subunit epitope, said antibodies being labelled with alkaline phosphatase,
  (ii) anti-$\beta$ subunit HCG monoclonal antibodies conjugated with fluorescein isothiocyanate (FITC), and if the antibodies of said component
    (i) cross-react with luteinising hormone (LH)
  (iii) anti-LH antibodies;

(b) adding to the assay system a solid phase having bound thereto anti-FITC antibodies;

(c) after a suitable incubation time separating the solid phase from the liquid phase;

(d) the separated solid phase in the presence of an appropriate substrate buffer for the alkaline phosphatase label containing phenolphthalein monophosphate and stopping the enzyme reaction after a suitable length of time;

(e) measuring the absorbance of the supernatant at 490 nm and calculating the true absorbance at 554 nm by utilizing the result of linear regression analysis of absorbance measurements obtained with phenolphthalein standards at 490 nm and 544 nm within the linear range of the detector; and (f) determining from said calculated absorbance at 554 nm the combined amount of HCG and free HCG-$\beta$ subunit in said sample.

* * * * *

UNITED STATES PATENT AND TRADEMARK OFFICE
CERTIFICATE OF CORRECTION

PATENT NO. : 4,914,023

DATED : April 3, 1990

INVENTOR(S) : Roger Philo

It is certified that error appears in the above-identified patent and that said Letters Patent is hereby corrected as shown below:

In claim 7, paragraph (b), change "an i-FITC" to --anti-FITC--.
In claim 8, line 1, change "4" to --1--; paragraph (d) insert --incubating-- before "the separated solid"

Signed and Sealed this

Fourteenth Day of May, 1991

Attest:

HARRY F. MANBECK, JR.

Attesting Officer     Commissioner of Patents and Trademarks